United States Patent [19]

Nakajima et al.

[11] Patent Number: 5,098,606
[45] Date of Patent: Mar. 24, 1992

[54] EMULSIFIED COMPOSITION

[75] Inventors: Hideo Nakajima; Miyuki Okabe; Satoshi Tomomasa, all of Yokohama, Japan

[73] Assignee: Shiseido Company Ltd., Tokyo, Japan

[21] Appl. No.: 609,507

[22] Filed: Nov. 6, 1990

[30] Foreign Application Priority Data

Nov. 20, 1989 [JP] Japan .................................. 1-302443

[51] Int. Cl.$^5$ ............................................ B01D 17/00
[52] U.S. Cl. .................................... 252/358; 252/356; 514/938; 424/450; 264/4.1
[58] Field of Search ..................... 252/312, 358, 356; 514/938; 424/450; 264/4.1

[56] References Cited

U.S. PATENT DOCUMENTS

| | | |
|---|---|---|
| 4,331,654 | 5/1982 | Morris . |
| 4,647,586 | 3/1987 | Mizushima et al. ............... 514/532 |
| 4,708,861 | 11/1987 | Popescu et al. ................... 424/1.1 |
| 4,797,285 | 1/1989 | Barenholz et al. ................. 424/450 |
| 4,804,539 | 2/1989 | Guo et al. ......................... 424/450 |
| 4,835,002 | 5/1989 | Wolf et al. ........................ 426/450 |
| 4,873,088 | 10/1989 | Mayhew et al. ................... 424/450 |
| 4,920,016 | 4/1990 | Allen et al. ........................ 424/450 |

FOREIGN PATENT DOCUMENTS

| | | |
|---|---|---|
| 0171084 | 2/1986 | European Pat. Off. . |
| 0315079 | 5/1989 | European Pat. Off. . |
| 0361928 | 4/1990 | European Pat. Off. . |
| 2494992 | 6/1982 | France . |

OTHER PUBLICATIONS 89-204085, "Anticancer Drug Contain Fat Emulsion Benzo . . . ", Derwent File Supplier WPTL, Derwent Pub. & JP-A-1 143 834.
98:221540n, Beyer, "Microemulsions", Pharmarmaceuticals, vol. 98, 1983, and whole article Pharmazie in unserer Zeit, No. 2 (1983).

*Primary Examiner*—Stephen J. Lechert, Jr.
*Assistant Examiner*—N. Bhat
*Attorney, Agent, or Firm*—Sprung, Horn, Kramer & Woods

[57] ABSTRACT

An emulsified composition comprising:
(A) a lipid soluble drug and a lipid;
(B) a sugar and/or a sugar alcohol;
(C) water;
(D) a water soluble nonionic surfactant having a molecular weight of 1000 or more, or a phospholipid and a water soluble nonionic surfactant having a molecular weight of 1000 or more;

where (A)/(D) is 0.5 to 5 (weight ratio), and the emulsified particles in the composition have an average particle size of 0.010 to 0.070 μm.

7 Claims, 2 Drawing Sheets

EMULSIFIED COMPOSITION

BACKGROUND OF THE INVENTION

1. Field of the Invention

The present invention relates to an improvement of an emulsified composition, particularly to an emulsified composition utilized as a preparation for a parenteral administration.

2. Description of the Related Art

Various emulsified compositions are used in the fields of, for example, pharmaceuticals and quasi-drugs, and as such an emulsified composition, a fat emulsion for an intravenous injection comprising lipid spheres with an average particle size of about 0.2 μm dispersed in an aqueous phase, is known in the art. This composition is generally obtained by an emulsification by a high pressure homogenizer, using lecithin as the emulsifier, and is utilized as a preparation for a nutrient supplementation of a patient or for a parenteral administration of a lipid soluble drug.

Particularly, this compound is effective as a preparation for an intravenous injection of a lipid soluble drug which cannot be intravenously injected as an aqueous solution, and is utilized as a drug delivery system.

Recent studies of passively or actively oriented drug delivery systems with microspheres have found that, when administered intravenously, particles of 0.100 to 2.000 μm are intraarterially or intraperitoneally incorporated rapidly from the blood stream by macrophages in the reticuloendothelial system, to be localized at the lysosomes of Kupffer's cells in the liver, and particles of 0.050 μm pass through the liver endothelial system and are thought to be gathered probably at the tumor tissue (see: Pharmacy International 2 (3) 1984). From the above standpoint, a fat emulsion for an intravenous injection with an average particle size of 0.2 μm, which is injected into the reticuloendothelial system, particularly the liver, is not satisfactory as a preparation for a parenteral administration of a lipid soluble drug, and the preparation of particles of 0.050 μm or less, which can be administered parenterally, is also a very important preparation technique.

As a compound which can be parenterally administered, the fat emulsion for intravenous injection as mentioned above is known in the art, but the preparation of parenterally administrable particles of 0.050 μm or less, i.e., nano-lipid spheres, in this system is very difficult, and this problem has been studied by researchers.

SUMMARY OF THE INVENTION

Accordingly, the objects of the present invention are to eliminate the above-mentioned disadvantages of the prior art and to provide an emulsified composition having an excellent stability and having lipid spheres with an average particle size of 0.010 to 0.070 μm dispersed in the aqueous phase.

Other objects and advantages of the present invention will be apparent from the following description.

In accordance with the present invention, there is provided an emulsified composition comprising:
(A) a lipid soluble drug and a lipid;
(B) a sugar, a sugar alcohol, or a mixture thereof
(C) water;
(D) a water soluble nonionic surfactant having a molecular weight of 1000 or more, or a phospholipid and a water soluble nonionic surfactant having a molecular weight of 1000 or more; wherein (A)/(D)=0.5 to 5 (weight ratio), and having an average particle size of 0.010 to 0.070 μm.

BRIEF DESCRIPTION OF THE DRAWINGS

The present invention will be better understood from the description set forth below with reference to the accompanying drawings, wherein.

DESCRIPTION OF THE PREFERRED EMBODIMENTS

Figure 1:
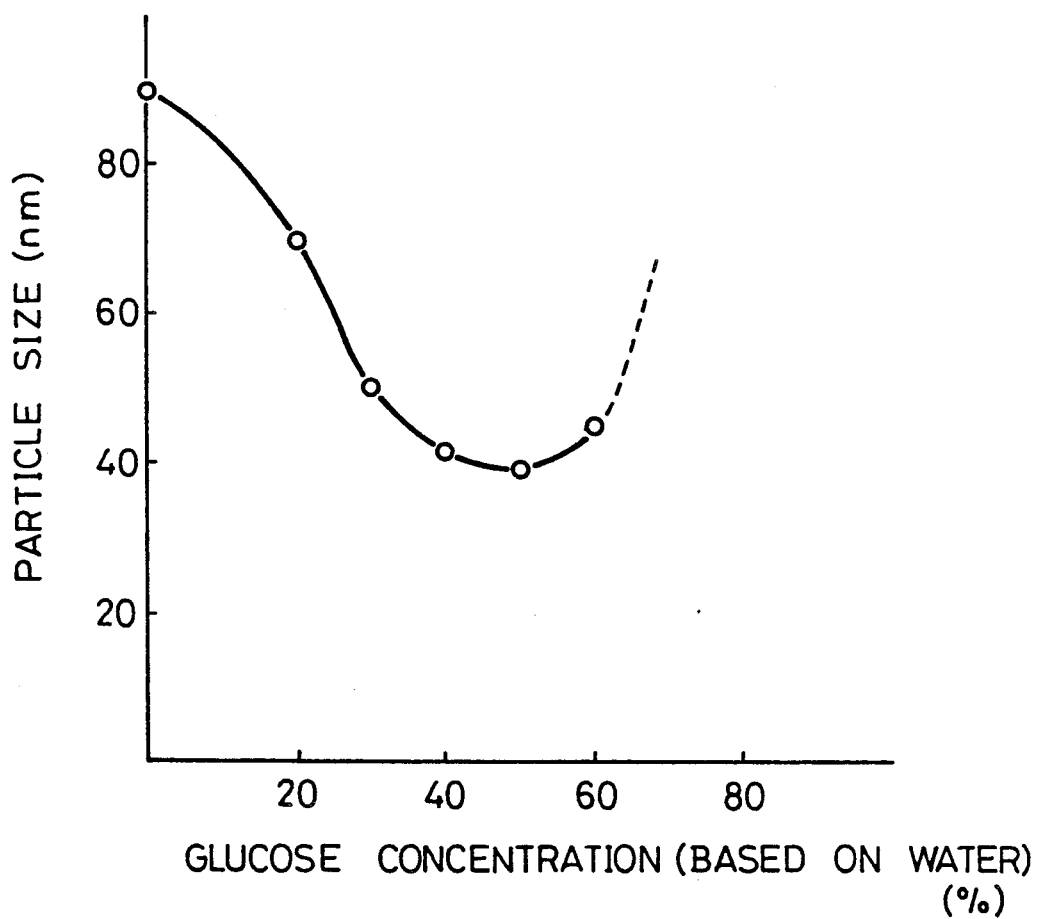
FIG. 1 is an illustration showing the relationship between the sugar or sugar alcohol concentration and particle size.

According to the present invention, a stable emulsified composition having emulsified particles of the desired size, i.e., lipid spheres of 0.010 to 0.070 μm, can be easily obtained by adding a sugar and/or a sugar alcohol, a phospholipid and a water soluble nonionic surfactant having a molecular weight of 1000 or more, preferably 1500 to 20000, or a water soluble nonionic surfactant having a molecular weight of 1000 or more, preferably 1500 to 20000.

The average particle sizes mentioned herein were all measured by the dynamic light scattering method; specifically, by NIDOMP-270 (HIAC/ROYCO).

The lipid usable as the component (A) in the present invention includes vegetable oils such as soybean oil, corn oil, safflower oil, cottonseed oil, and coconut oil, synthetic or semi-synthetic mono-, di-and tri-glycerides, sterols such as cholesterol and kenodeoxycholinic acid, cholesterol esters such as cholesteryl linoleate and cholesteryl caprylate, and monoesters such as oleyl oleate, ethyl linoleate, and ethyl laurate, which may be used alone or in combination. In general, when the carbon number of the lipid is smaller, the drug is better dissolved, but the stability of the emulsification is adversely affected. Accordingly, when a mono-, di-, tri-glyceride and/or a monoester having 33 or less, preferably 18 to 33 carbon atoms and/or a monoester having 22 or less, preferably 16 to 22 carbon atoms is used, 1% or more of a triglyceride having 45 or more carbon atoms and/or a monoester having 26 or more carbon atoms must be contained in the lipid. This is because, if an emulsified composition is prepared by using a mono-, di-, or tri-glyceride having 33 or less carbon atoms and/or a monoester having 22 or less carbon atoms, the stability thereof with a lapse of time is poor, and thus the particle size will be enlarged.

The lipid soluble drug usable in the present invention may be any drug soluble in the above-mentioned lipid, including, for example, antitumor agents such as mitomycin, bleomycin, doxorvicin, hexamethylmelamine, futrafuroleic acid ester, and dilauric acid ester of 5-FU, antibacterial agents such as penicillin, erythromycin, cephalosporin, streptomycin, kanamycin, tetracycline, chloramphenicol, isoniazide, cycloserine, amphoterin B, and glyseofluvin, antifungal agents, non-steroidal antiphlogistic agents such as salicylate, indomethacin, aminopyrine, phenacetin, ibuprofen, flulubiprofen, ketoprofen, and diclofenac, hormones such as prostaglandin and synthetic steroids, immune controllers such as cyclosporin, and lipid soluble vitamins such as vitamin A, vitamin D, and vitamin E.

Although there are no limitations to the ratio of the lipid soluble drug to the lipid, the ratio is preferebly 0.01 to 100, more preferably 9 to 1, so long as the drug is dissolved in the lipid.

The sugar usable in the present invention may include arabinose, xylose, glucose, galactose, mannose, fructose, lactose, trehalose, sucrose, maltose, and rhaffinose. Examples of the sugar alcohols are sorbitol and maltitol.

The phospholipid and the water soluble nonionic surfactant having a molecular weight of 1000 or more function as the emulsifier.

The phospholipid usable in the present invention may include lecithin derived from yolk or vegetable seed, for example, yolk lecithin, soybean lecithin, hydrogenated products thereof, phosphatidylcholine, phosphatidylethanolamine, phosphatidylinositol, phosphatidylserine, sphingomyelins, phosphatidic acid, and phytoglycolipid.

Examples of the nonionic surfactant are polyoxyethylene (hereinafter called POE) sorbitane fatty acid esters such as POE sorbitane monooleate, POE sorbitane monostearate, and POE sorbitane trioleate, POE sorbitol fatty acid esters such as POE sorbitol monooleate, POE sorbitol pentaoleate, and POE sorbitol monostearate, POE glycerine fatty acid esters such as POE glycerine monostearate, POE fatty acid esters such as POE monooleate, POE distearate, and POE dioleate, POE alkyl ethers such as POE oleyl ether, POE stearyl ether, and POE behenyl ether, POE sterol ethers such as POE cholestanol ether and POE cholesterol ether, POE-POP alkyl ethers such as POE-POP block polymers, and POE-POP cetyl ether, POE castor oil such as POE castor oil, or hydrogenated castor oil derivatives and polyglycerine fatty acid esters, such as decaglycerine dioleate, and among the above, those having molecular weights of 1000 or more may be employed. Further, preferably the molecular weight is 1500 or more, more preferably 1500 to 20000. Particularly preferably, POE stearyl ether, POE oleyl ether, POE monostearate, POE monooleate, POE cholestanol ether, POE cholesterol ether, and POE hydrogenated castor derivatives are included.

Here, the molecular weight of the nonionic surfactant is made 1000 or more because a nonionic surfactant with a molecular weight of less than 1000 causes an extreme irritation of a living body, and hemolysis may sometimes occur when it is employed as the injection solution.

Also, a water soluble nonionic surfactant with a molecular weight of 1000 or more may be used alone, but it is more preferable to use a phospholipid in combination. The weight ratio of a phospholipid to a nonionic surfactant is preferably 9.5:0.5 to 1:9, more preferably 9:1 to 2:8, most preferably 8:2 to 3:7.

The emulsified composition of the present invention has a particle size of 0.010 to 0.070 μm, preferably 0.050 or less, more preferably 0.040 μm or less.

The particle size of the emulsified composition in the present invention depends on the weight ratio of (A) and (D), and the particle size tends to be smaller when the (A)/(D) is lower. Therefore, when the ratio is more than 5, an emulsified composition with an average particle size of 0.070 μm or less cannot be obtained, but to obtain an emulsified composition with an average particle size of 0.050 μm or less, which is a preferable particle size, the ratio thereof must be 3 or less. Nevertheless, an administration of a large amount of a surfactant functioning as the emulsifier will have a very adverse affect on the blood vessel system and blood, and thus it is important to obtain smaller particles with the use of as small as an amount of a surfactant possible. Therefore, a preferable ratio is 1.0 or more.

In the present invention the weight ratio of (A)/(D) is preferably 0.5 to 5, more preferably 1 to 3.

In the present invention, the weight ratio of sugar and/or sugar alcohol to water during the emulsification is preferably made 2:8 to 7:3, more preferably 3:7 to 6:4, most preferably 4:6 to 5:5.

When the ratio of sugar and/or sugar alcohol to water during emulsification is less than 2:8, an effect of the addition thereof will not be exhibited, and when it is more than 7:3, the effect of making the particle size smaller cannot be fully obtained.

The preferable weight ratio of the components (A)/(B)/(C)/(D) of the present invention is 1 to 30/45 to 50/20 to 92/0.5 to 20, more preferably 3 to 20/4.5 to 40/40 to 90/1 to 15.

The average particle size of the emulsified composition obtained by the present invention is 0.010 to 0.070, preferably 0.010 to 0.050 μm, and more preferably 0.015 to 0.040 μm.

Also, in the present invention, by effecting an emulsification capable of giving a strong shearing force, such as with a high pressure homogenizer or a sonication emulsifier, lipid spheres with particle sizes of 0.050 μm or less can be obtained.

For example, when preparing an emulsified composition with an (A)/(D) of 3, when the emulsification is effected without an addition of sugar and/or sugar alcohol, even if the emulsification by a high pressure homogenizer is varied and adjusted, it is very difficult to obtain lipid spheres with particle sizes of 0.100 μm or less, and impossible to obtain those with 0.070 μm or less. Nevertheless, when an emulsification is effected at a weight ratio of sugar and/or sugar alcohol during an emulsification at a ratio of 2:8 to 7:3, lipid spheres with particle sizes of 0.050 μm or less can be obtained. On the other hand, at an (A)/(D) of 1, when sugar and/or sugar alcohol is not used, it is very difficult to obtain lipid spheres with particle sizes of 0.070 μm or less, and those of 0.050 μm or less cannot be obtained. Nevertheless, when an emulsification is effected at a weight ratio of sugar and/or sugar alcohol during an emulsification at a ratio of 2:8 to 7:3, lipid spheres with particle sizes of 0.020 μm or less can be obtained.

When a high pressure homogenizer is used, preferably the emulsification is carried out under a pressure of 200 atm. or higher, and further, to obtain particles of 0.050 μm or less, preferably the emulsification is carried out at a temperature of 70° C. or lower and under a pressure of 500 atm. or higher. To obtain even smaller particles, preferably the emulsification is carried out at a temperature of 50° C. or lower under a pressure of 800 atm. or higher.

This emulsified composition can be used also after emulsification, by diluting it to a predetermined sugar and/or sugar alcohol concentration before use.

The predetermined sugar and/or sugar concentration in the present invention depends on the use, but is preferably an isotonic concentration or higher.

The emulsified composition of the present invention can formulate various parenterally administratable components within the range which does not impair the effect of the present invention, if necessary, in addition to the essential components. Among such components, the aqueous phase components include amino acids and related compounds, electrolytes, and water soluble vitamins.

As described above, in the prior art only fine particles having an average particle size of a micro-order could be obtained, but in the present invention, stable fine particles of a nano-order can be obtained.

The lipid nano-spheres of such an emulsion composition, particularly those with particle sizes of 0.050 $\mu$m or less, are considered to pass through the reticuloendothelial system when administered intravenously, intraarterily or intraperitoneally, to gather at tumor tissues, and can be utilized as a novel and effective preparation for a parenteral administration, and as a base of a drug delivery system of an antitumor agent.

As described in detail above, according to the present invention, since a lipid soluble drug and a lipid, a sugar and/or a sugar alcohol, water, a phospholipid and a water soluble nonionic surfactant having a molecular weight of 1000 or more, or a water soluble nonionic surfactant having a molecular weight of 1000 or more, are formulated, an emulsion having stable lipid nano-spheres with an average particle size of 0.010 to 0.070 $\mu$m can be obtained.

EXAMPLES

The present invention will now be further illustrated by, but is by no means limited to, the following Examples.

Relationship Between Concentration of Aqueous Glucose Solution and Particle Size First, the relationship between the ratio of glucose to water during emulsification and the particle size is explained.

A formulation of 16 parts by weight of 1% soybean oil solution of nonyloxycarbonylmitomycin C, 6 parts by weight of yolk phosphatidylcholine, 2 parts by weight of POE(50) oleyl ether, and 76 parts by weight of an aqueous glucose solution was treated 40 times by a microfluidizer (Microfluidisc) under an emulsification pressure of 800 atm., to obtain an emulsified composition, and the particle sizes of the emulsion compositions with various concentrations of the aqueous glucose solution were measured.

The results are shown in FIG. 1, and as apparent from the Figure, the particle size is made smaller by an addition of glucose, reaches a maximum value at an approximately 50% concentration, and is again increased as the concentration becomes higher. Accordingly, it can be understood that an addition of glucose is very effective when attempting to obtain small size particles, but if the glucose concentration becomes 70% or higher, the emulsification becomes difficult due to an increase of the viscosity.

Relationship Between Ratio of Phospholioid to Nonionic Surfactant and Particle Size After 5.0% by weight of tocopherol acetate, 15.0% by weight of soybean oil, 10% by weight of an emulsifier, 40% by weight of water, and 30.0% by weight of glucose were preliminarily emulsified, an emulsified product was obtained 30 treatments by a microfluidizer under an emulsification pressure of 1000 atm. at 50° C.

The composition ratios and the particle sizes at that time are shown in Table 1.

TABLE 1

| Lecithin:POE(50) stearyl ether | Particle size ($\mu$m) |
| --- | --- |
| 1:0 | 0.075 |
| 0.9:0.1 | 0.039 |
| 0.75:0.25 | 0.035 |
| 0.5:0.5 | 0.035 |
| 0.25:0.75 | 0.040 |
| 0:1 | 0.045 |

From the above Table 1, it can be understood that the particle size becomes finer in the case of a mixture of lecithin (purified yolk lecithin) and POE(50) stearyl ether (water soluble nonionic surfactant having a molecular weight of 1000 or more), compared with the case where each component is used alone, becomes particularly very fine when lecithin is used at a ratio of 75 to 50%, and that it is difficult to obtain an emulsified composition with particle sizes of 70 nm or less with lecithin alone.

Relationship Between (A)/(D) and Average Particle Size

First, the relationship between the weight ratio of the lipid soluble drug and the lipid (A) to the phospholipid and the water soluble nonionic surfactant (D) having a molecular weight of 1000 or more and the average particle size is explained.

The recipes during emulsification were prepared as shown in Table 2, each recipe was treated 30 times by a microfluidizer under an emulsification pressure of 1000 atm., and the average particle size thereof was measured. The formulation amounts are respectively in % by weight.

TABLE 2

| (A)/(D) ratio | (A) | (D) | Aqueous 50% glucose solution |
| --- | --- | --- | --- |
| 1 | 12 | 12 | 76 |
| 2 | 18 | 9 | 73 |
| 3 | 24 | 8 | 68 |
| 4 | 24 | 6 | 70 |
| 5 | 25 | 5 | 70 |
| 6 | 24 | 4 | 72 |
| 7 | 28 | 4 | 68 |

Figure 2:
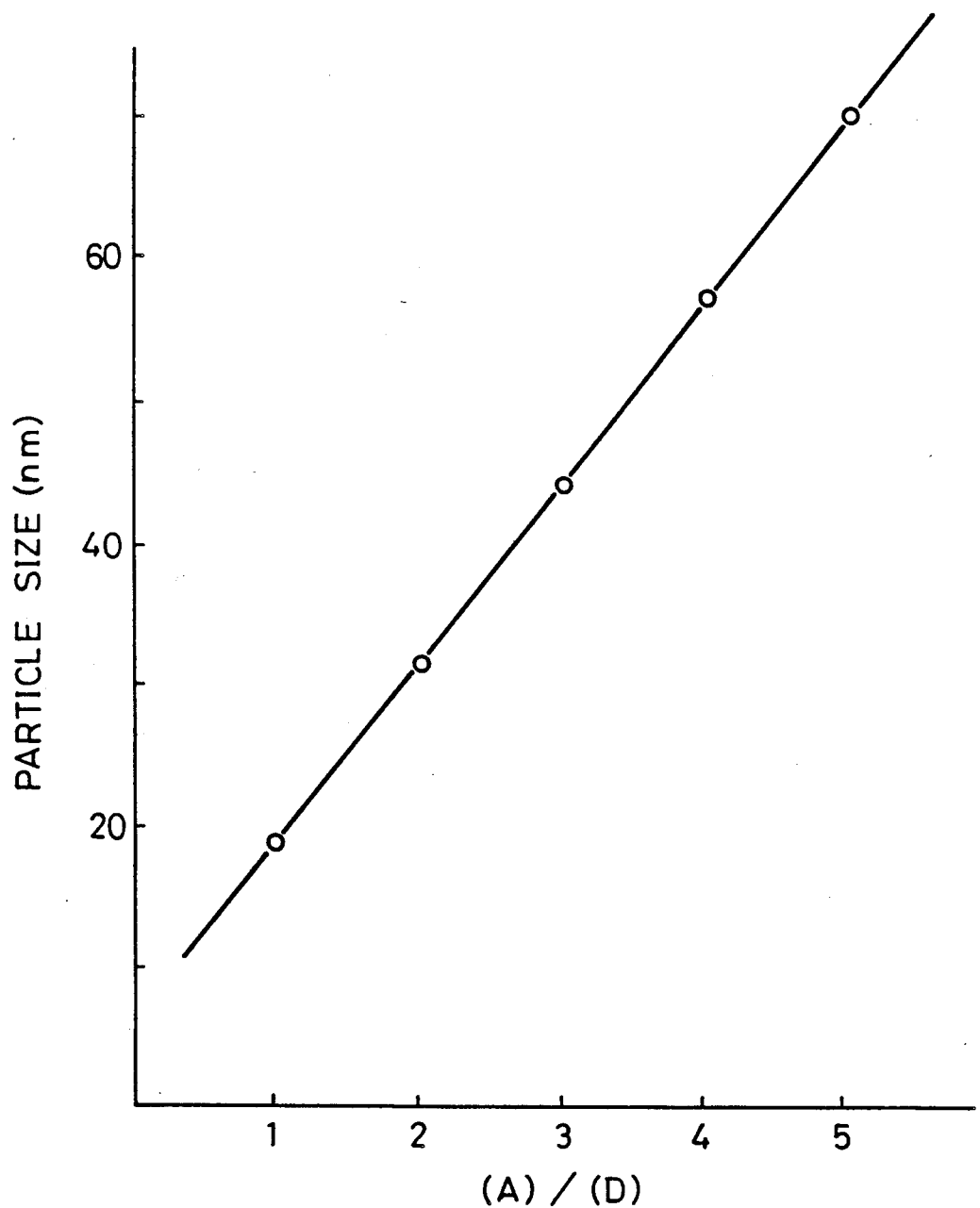
FIG. 2 is an illustration showing the relationship between the particle size and the weight ratio of the lipid soluble drug and the lipid (A) to the phospholipid and the water soluble nonionic surfactant (D) (i.e., (A)/(D) ratio).

FIG. 2 shows the relationship between (A)/(D) and the particle size when using 1% soybean oil solution of nonyloxycarbonyl MMC as the component A (lipid soluble drug and lipid) and a 3:1 mixture of yolk phosphatidylcholine and POE(50) monostearyl ester as the component D (emulsifier).

As apparent from the Figure, (A)/(D) and the particle size have a substantially direct proportional relationship, and at an (A)/(D) of about 5, the particle size becomes 70 nm (0.070 $\mu$m). Also, the particle size becomes too large at a higher ratio.

From these results, it can be understood that the (A)/(D) is closely related to the particle size, and at a ratio of 5 or less, the desired particle size of 70 nm can be obtained, and further, that the particle size becomes smaller substantially in direct proportion to the (A)/(D).

EXAMPLE 1

After 14 parts of a soybean oil containing 1% by weight of diclofenac, 36 parts by weight of water, 36 parts by weight of mannose, and 14 parts by weight of POE 40 cholestanol ether were preliminarily emulsified, the emulsion was emulsified by a 40 times treatment with a microfluidizer at 50° C. under a pressure of 1000 atm., followed by an addition of 100 parts by weight of water, and sterilization by passing through a 0.22 μm membrane filtration machine. The emulsified compositions immediately after preparation had a particle size of 0.025 μm and were transparent. An evaluation of the state and the particle size thereof after being left to stand at room temperature for 3 months showed that no change was observed.

EXAMPLE 2

After 18 parts by weight of a soybean oil containing 2% by weight of dexamethazone palmitate, 36 parts by weight of water, 36 parts by weight of sorbitol, and 10 parts by weight of POE(40) stearyl ether were preliminarily emulsified, emulsification was effected at 50° C. and a 30 times treatment and a 30 times treatment, by a microfluidizer under a pressure of 1000 atm., followed by an addition of 100 parts by weight of water, and was sterilized by passing through a 0.22 μm membrane filtration machine. The emulsified compositions immediately after preparation had a particle size of 0.037 μm and were substantially transparent. An evaluation of the state and the particle size thereof after being left to stand at room temperature for 3 months showed that no change was observed.

EXAMPLE 3

After 24 parts by weight of a soybean oil containing 5% by weight of 5-FU palmitate, 42 parts by weight of water, 26 parts by weight of maltose, and 8 parts by weight of POE(40) stearyl ether were preliminarily emulsified, an emulsification was effected at 50° C. and a 30 times treatment by a microfluidizer under a pressure of 800 atm., followed by an addition of 100 parts by weight of water, and sterilized by passing through a 0.22 μm membrane filtration machine. The emulsified compositions immediately after preparation had a particle size of 0.062 μm and were substantially transparent. An evaluation of the state and the particle size thereof after being left to stand at room temperature for 3 months showed that no change was observed.

EXAMPLE 4

After 2 parts by weight of futraful palmitate, 1 part by weight of soybean oil, 15 parts by weight of ethyl oleate, 42 parts by weight of water, 30 parts by weight of maltitol, 5 parts by weight of purified yolk, and 5 parts by weight of POE 60 hardened castor oil were preliminarily emulsified, an emulsification was effected at 50° C. and a 30 times treatment by a microfluidizer under a pressure of 1000 atm., followed by an addition of 100 parts by weight of water, and sterilized by passing through a 0.22 μm membrane filtration machine. The emulsified compositions immediately after preparation had a particle size of 0.038 μm and were substantially transparent. An evaluation of the state and the particle size thereof after being left to stand at room temperature for 3 months showed that no change was observed.

EXAMPLE 5

After 1 part by weight of cyclosporin, 1 part by weight of soybean oil, 14 parts by weight of ethyl laurate, 34 parts by weight of water, 40 parts by weight of arabinose, 7 parts by weight of purified yolk lecithin, and 3 parts by weight of POE 50 oleyl ether were preliminarily emulsified, emulsification was effected at 50° C. and a 50 times treatment by a microfluidizer under a pressure of 1000 atm., followed by an addition of 100 parts by weight of water, and sterilized by passing through a 0.22 μm membrane filtration machine. The emulsified compositions immediately after preparation had a particle size of 0.018 μm and were substantially transparent. An evaluation of the state and the particle size thereof after being left to stand at room temperature for 3 months showed that no change was observed.

EXAMPLE 6

After 2 parts by weight of erythromycin, 1 part by weight of soybean oil, 27 parts by weight of glycerine tricaprylate, 44 parts by weight of water, 26 parts by weight of xylose, 1 part by weight of purified yolk lecithin, and 6 parts by weight of POE 30 cholestanol ether were preliminarily emulsified, an emulsification was effected at 70° C. and a 30 times treatment by a microfluidizer under a pressure of 800 atm., followed by an addition of 100 parts by weight of water, and sterilized by passing through a 0.22 μm membrane filtration machine. The emulsified compositions immediately after preparation had a particle size of 0.062 μm and were substantially transparent. An evaluation of the state and the particle size thereof after being left to stand at room temperature for 3 months showed that no change was observed.

EXAMPLE 7

After 25 parts by weight of a soybean oil containing 1/1000% by weight of prostaglandin E2, 36 parts by weight of water, 29 parts by weight of glucose, and 10 parts by weight of POE 50 stearyl ether were preliminarily emulsified, an emulsification was effected at 70° C. and a 20 times treatment by a microfluidizer under a pressure of 1000 atm., followed by an addition of 100 parts by weight of water, and sterilized by passing through a 0.22 μm membrane filtration machine. The emulsified compositions immediately after preparation had a particle size of 0.050 μm and were substantially transparent. An evaluation of the state and the particle size thereof after being left to stand at room temperature for 3 months showed that no change was observed.

EXAMPLE 8

After 21 parts by weight of tocopherol acetate, 2 parts by weight of soybean oil, 8 parts by weight of purified yolk lecithin, 1 part by weight of POE 50 monooleate, 45 parts by weight of water, and 25 parts by weight of glucose were preliminarily emulsified, an emulsification was effected at 50° C. and a 20 times treatment by a microfluidizer under a pressure of 1000 atm., followed by an addition of 100 parts by weight of water, and sterilized by passing through a 0.22 μm membrane filtration machine. Further, 300 parts by weight of a sterilized water were added to make up an isotonic solution, to thus obtain a vitamin E agent for an intravenous injection. The agent was found to have an emulsified particle size of 0.050 μm.

An evaluation of the state and the particle size thereof after being left to stand at room temperature for 3 months showed that no change was observed.

EXAMPLE 9

After 0.2 part by weight of nonyloxycarbonylmitomycin C, 18.8 parts by weight of soybean oil, 5 parts by weight of phosphatidylcholine, 4 parts by weight of POE(50) monostearate, 37 parts by weight of water, and 35 parts by weight of glucose were preliminarily emulsified, an emulsification was effected at 50° C. and a 30 times treatment by a microfluidizer under a pressure of 1000 atm., followed by an addition of 100 parts by weight of water, and sterilized by passing through a 0.22 μm membrane filtration machine. Further, 300 parts by weight of a sterilized water were added to make up an isotonic solution, to thus obtain a nonyloxycarbonylmitomycin C agent for intravenous injection. The agent was found to have an emulsified particle size of 0.39 μm.

An evaluation of the state and the particle size thereof after being left to stand at room temperature for 3 months showed that no change was observed.

EXAMPLE 10

After 0.1 part by weight of amphotericin B, 9.9 parts by weight of soybean oil, 8 parts by weight of yolk phosphatidylcholine, 2 parts by weight of POE (30) oleyl ether, and 40 parts by weight of fructose were preliminarily emulsified, emulsification was effected at 40° C. and a 50 times treatment by a microfluidizer under a pressure of 1000 atm., followed by an addition of 100 parts by weight of water, and sterilized by passing through a 0.22 μm membrane filtration machine. Further, 100 parts by weight of a sterilized water were added, to thereby obtain an amphotericin B intravenous injection. The agent was found to have an emulsified particle size of 0.018 μm.

An evaluation of the state and the particle size thereof after being left to stand at room temperature for 3 months showed that no change was observed.

We claim:

1. An emulsified composition comprising:
   (A) a lipid soluble drug and a lipid;
   (B) a material selected from the group consisting of a sugar, a sugar alcohol and a mixture thereof;
   (C) water;
   (D) a material selected from the group consisting of a water soluble nonionic surfactant having a molecular weight of 1000 or more, and a phospholipid and a water soluble nonionic surfactant having a molecular weight of 1000 or more;

wherein (A)/(D) is 0.5 to 5 (weight ratio), the emulsified particles in the composition having an average particle size of 0.010 to 0.070 μm.

2. An emulsified composition as claimed in claim 1, wherein the ratio (weight ratio) of the sugar, sugar alcohol or a mixture thereof to water during emulsification is 2:8 to 7:3.

3. An emulsified composition as claimed in claim 1, wherein the lipid is at least one member selected from the group consisting of vegetable oils, glycerides, sterols, cholesterol esters, and monoesters.

4. An emulsified composition as claimed in claim 1, wherein the phospholipid is at least one member selected from the group consisting of lecithins derived from yolk and vegetable seeds, the hydrogenated products thereof, phosphatidylcholine, phosphatidylethanolamine, phosphatidylinositol, phosphatidylserine, sphingomyelins, phosphatidic acid, and phytoglycolipid.

5. An emulsified composition as claimed in claim 1, wherein the water soluble nonionic surfactant is at least one member selected from the group consisting of polyoxyethylene sorbitane fatty acid esters, polyoxyethylene sorbitol fatty acid esters, polyoxyethylene glycerine fatty acid esters, polyorgethylene fatty acid esters, polyoxyethylene alkyl ethers, polyoxyethylene sterol ethers, polyoxyethylene-polyoxypropylene alkyl ethers, polyoxyethylene castor oils, hydrogenated castor oil derivatives, cholesterol derivative and polyglycerine fatty acid esters.

6. An emulsified composition as claimed in claim 1, wherein the weight ratio of the phospholipid to the nonionic surfactant is 9.5/0.5 to 1/9.

7. An emulsified composition as claimed in claim 1, when the weight ratio of the components (A)/(B)/(C)/(D) is 1 to 30/5 to 50/20 to 92/0.5 to 20.

* * * * *